United States Patent
Knuuttila et al.

(10) Patent No.: US 9,677,011 B2
(45) Date of Patent: Jun. 13, 2017

(54) PROCESS AND APPARATUS FOR PRODUCING HYDROCARBONS BY HYDROGENATING A TERPENE FEED

(75) Inventors: Pekka Knuuttila, Porvoo (FI); Jaakko Nousiainen, Lappeenranta (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 175 days.

(21) Appl. No.: 13/382,823

(22) PCT Filed: Jul. 2, 2010

(86) PCT No.: PCT/FI2010/050573
§ 371 (c)(1),
(2), (4) Date: Jan. 6, 2012

(87) PCT Pub. No.: WO2011/004066
PCT Pub. Date: Jan. 13, 2011

(65) Prior Publication Data
US 2012/0108675 A1    May 3, 2012

(30) Foreign Application Priority Data

Jul. 7, 2009   (FI) .................................... 20095767
Feb. 2, 2010   (FI) .................................... 20105092

(51) Int. Cl.
*C10G 45/08*      (2006.01)
*C10G 45/02*      (2006.01)
(Continued)

(52) U.S. Cl.
CPC .............. *C10G 45/02* (2013.01); *C10G 3/46* (2013.01); *C10G 3/50* (2013.01); *C10G 45/58* (2013.01);
(Continued)

(58) Field of Classification Search
CPC .......... C10G 45/02; C10G 45/58; C10G 3/46; C10G 3/50; C10G 2300/202;
(Continued)

(56) References Cited

U.S. PATENT DOCUMENTS 2,654,711 A * 10/1953 Kirshenbaum et al. ...... 508/325
3,312,750 A *  4/1967 Berg et al. .................... 585/841
(Continued)

FOREIGN PATENT DOCUMENTS

| EP | 0 243 238 A1 | 10/1987 |
|---|---|---|
| EP | 0 267 833 A1 | 5/1988 |
| WO | WO 2009/156452 A2 | 12/2009 |

OTHER PUBLICATIONS

Casbas, Duprez, Ollivier: "Catalytic hydrodesulphurization of terpenes", Applied Catalysis, vol. 50, 1989, pp. 87-97 XP002614594.*
(Continued)

*Primary Examiner* — In Suk Bullock
*Assistant Examiner* — Philip Louie
(74) *Attorney, Agent, or Firm* — Cantor Colburn LLP

(57) ABSTRACT

The invention relates to a process and an apparatus for producing hydrocarbon components in the presence of a hydrodesulphurization catalyst. The components obtained by the process are suitable for use as fuel composition as such or as an additive in fuel compositions, and in cosmetics or pharmaceutical products.

17 Claims, 4 Drawing Sheets

(51) Int. Cl.
*C10G 45/58* (2006.01)
*C10G 3/00* (2006.01)

(52) U.S. Cl.
CPC ............... *C10G 2300/1014* (2013.01); *C10G 2300/202* (2013.01); *C10G 2300/207* (2013.01); *C10G 2400/02* (2013.01); *C10G 2400/04* (2013.01); *C10G 2400/08* (2013.01); *Y02P 30/20* (2015.11)

(58) Field of Classification Search
CPC ...... C10G 2300/207; C10G 2300/1014; C10G 2400/02; C10G 2400/04; C10G 2400/08
USPC ......................................................... 585/242
See application file for complete search history.

(56) References Cited

U.S. PATENT DOCUMENTS

| | | | |
|---|---|---|---|
| 3,441,497 A * | 4/1969 | Walter et al. | 208/15 |
| 4,108,917 A | 8/1978 | Wattimena | |
| 4,375,572 A | 3/1983 | Wideman | |
| 5,186,722 A * | 2/1993 | Cantrell et al. | 44/605 |
| 5,705,722 A | 1/1998 | Monnier et al. | |
| 2004/0000506 A1 | 1/2004 | Podrebarac et al. | |
| 2004/0230085 A1 | 11/2004 | Jakkula et al. | |
| 2005/0029162 A1 | 2/2005 | Shih et al. | |
| 2007/0267326 A1 | 11/2007 | De Almeida et al. | |
| 2009/0020089 A1 | 1/2009 | Ryder et al. | |

OTHER PUBLICATIONS

Casbas, Duprez, Ollivier. "Catalytic Hydrodesulphurization of Terpenes", Applied Catalysis, vol. 50, 1989, pp. 87-97. XP002614594.*
Mercier, B., Prost, J., and Prost, M., "The Essential Oil of Turpentine and Its Major Volatile Fraction (alpha- and beta-pinenes): A Review", International Journal of Occupational Medicine and Environmental Health 2009; 22(4):331-342.*
Tracy, N., Chen, D., Crunkleton, D., and Price, G., "Hydrogenated monoterpenes as diesel fuel additives", Fuel, 2009, pp. 2238-2240.*
Grafflin, W., "System of Nomenclature for Terpene Hydrocarbons Acyclics, Monocyclics, Bicyclics", Advances in Chemistry, American Chemical Society, 1955, p. 1-11.*
Casbas et al. "Catalytic Hydrodesulphurization of Terpenes", XP-002614594, Applied Catalysis, vol. 50, pp. 89-97, 1989).*
Towler, G. and Sinnott, R.,"Chemical Engineering Design Principles, Practice and Economics of Plant and Process Design", Instrumentation and Process Control, Second Edition, Chapter 5, p. 251-277).*
EP 0267833 Description English Machine Translation obtained from EPO, 2016, pp. 1-6.*
Finnish Search Report, dated Dec. 31, 2010, issued in Finnish Application No. 20105092.
Finnish Search Report, dated May 12, 2010, issued in Finnish Application No. 20095767.
International Search Report, dated Jan. 4, 2011, issued in PCT/FI2010/050573.
Written Opinion of the International Searching Authority, dated Jan. 4, 2011, issued in PCT/F12010/050573.
Casbas et al., "Catalytic Hydrodesulphurization of Terpenes", XP-002614594, Applied Catalysis, vol. 50, pp. 87-97, 1989.

* cited by examiner

PROCESS AND APPARATUS FOR PRODUCING HYDROCARBONS BY HYDROGENATING A TERPENE FEED

FIELD OF THE INVENTION

The present invention relates to a process and an apparatus for producing hydrocarbons. More particularly, the invention relates a conversion of terpenes to hydrocarbon compounds which are useful as various fuel grade compositions as such, or as fuel blending components.

BACKGROUND OF THE INVENTION

There is an increasing interest on the use of hydrocarbon components of biological origin from renewable sources in fuels to replace the fossil starting materials. The use thereof is highly desirable for environmental reasons. There is a lot of literature relating to production of fuel composition from biological starting materials like vegetable oils, such as tall oil.

US 2004/0230085 A1 discloses a process for producing hydrocarbon components from wood-based tall oil by a two-step procedure in which a fatty acid fraction of tall oil (TOFA) is subjected to a hydrodeoxygenation step to hydrogenate TOFA in the presence of a desulphurization catalyst and then to an isomerization step to branch the hydrocarbon chain. The products obtained from the isomerization are predominantly i-paraffins which are suitable for use as components in diesel fuels. The hydrocarbon chain lengths suitable for diesel components are typically in the range of $C_9$-$C_{20}$.

US 2009/0020089 A1 discloses a fuel composition comprising at least a tetramethylcyclohexane and optionally an aromatic isoprenoid compound, and a monocyclic and acyclic hydrocarbon component. The fuel composition can be of petrol fuel grade, for example. The tetramethylcyclohexane is produced by hydrogenation of pinene in the presence of a hydrogenation catalyst. Pinene and the starting materials for the optional components included in the fuel composition are produced by microbiological methods using a host cell.

Tall oil is retrieved from the kraft pulping process of coniferous wood as a by-product. From the same process, also crude turpentine is extracted as a by-product. Chemical compositions of said substances differ from each other to a significant extent. Tall oil is mainly composed of fatty acids and resin acids with a chain length varying between $C_{12}$ to $C_{18}$, and fused ring systems as abietic acids and sitosterols, while the crude turpentine comprises an oil mixture of terpenes derived from pitch. Terpenes are a wide range of volatile hydrocarbons having a chemical formula of $C_{10}H_{16}$, including typically unsaturated mono- and bicyclic hydrocarbons. Crude turpentine, which contains terpenes, is formed in the kraft pulping process is generally referred to as crude sulphate turpentine (CST). The main terpene components included in the CST are α-pinene, β-pinene and and Δ-3-carene. The major component is typically α-pinene.

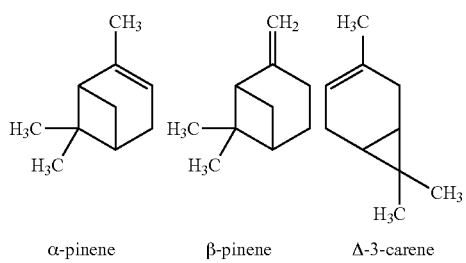

α-pinene  β-pinene  Δ-3-carene

The unsaturated bicyclic terpenes included in the turpentine, having the formulas given above, are too reactive as such for use as fuel components. Also, the high sulphur content of the turpentine prevents using it for fuel application.

Processes for converting terpenes to cymenes are previously known. In these processes, different types of catalysts are used for the conversion. For example, alkali metal carbonate catalysts, catalysts comprising noble metals or rare earth metals on a zeolite support and a palladium catalyst supported on activated carbon or alumina have been used.

CST comprising a large amount of terpene isomers also contains a relatively high amount of sulphur, up to 6%, as a contaminant. In order to be able to utilize the CST for further applications sulphur has to be removed from it. In EP 0267833 A1 sulphur is removed from the terpenes included in the crude turpentine through hydrogenation in the presence of a catalyst of cobalt and molybdenum oxides on an inorganic support. It is desired that any chemical transformation of the terpenes is avoided during the hydrodesulphurization procedure.

At present, the crude sulphate turpentine is processed for use as a solvent or odorants in pharmaceutical and cosmetic industry. However, a wide range of utilization of the turpentine is restricted because of the high level of sulphur, and no cost efficient processes for desulphurization and refining the turpentine are now present. Accordingly, a large amount of the crude sulphate turpentine is now burned without further processing.

BRIEF DESCRIPTION OF THE INVENTION

It has now been found that terpenes can be converted to various fuel grade components by a one-step process by using a conventional hydrodesulphurization (HDS) catalyst. The components obtained in the process of the invention can be used as fuel compositions as such or as fuel additives in the fuel compositions. Examples of the fuel compositions are diesel, gasoline, naphta and jet fuels.

For example, hydrocarbon components having a carbon number typical for gasoline components, varying from $C_4$ to $C_{10}$, are received from the process of the invention. Also, hydrocarbon components having a carbon number typical for diesel components, varying from $C_{10}$ to $C_{28}$, are received from the process of the invention. A part of the produced components can also be utilized in other products, such as in cosmetics or pharmaceutical products.

It has been specifically found that an amount of aromatics, especially paracymene obtained in the process, can be increased in an appropriate manner by controlling the process parameters. Paracymene has a particular value as a fuel component. Moreover, it can be utilized for cosmetics and in pharmaceutical industry.

Drawback of the known processes for producing paracymene from terpenes is that the catalytic activity of the catalysts used is destroyed by the presence of sulphur even at low concentrations.

In a specific embodiment of the invention, crude sulphate turpentine is used as a starting material. The crude sulphate turpentine may also comprise distillation bottoms products from turpentine distillation. As stated above, the high sulphur content of the turpentine prevents using it for fuel application. It was surprisingly found that terpenes can be converted in one single step to a form that contains only a small amount of sulphur, or to a form where the sulphur can be easily removed by using a conventional hydrodesulphurization catalyst while the crude sulphate turpentine is converted to valuable products useful in a fuel application. It is an advantage of the process that there is no need of any pretreatment procedure in order to remove sulphur from the CST prior to its further processing. In an embodiment, the invention thus provides a simple, efficient and economical process for the treatment of the crude sulphate turpentine to provide a product that is usable for fuel applications.

It is thus an object of the present invention to provide a process and an apparatus for producing hydrocarbon components which may be utilized as fuel components. The object of the invention is achieved by what is stated in the independent claims.

Another object of the invention is to provide a use of the hydrocarbon components obtained by the process of the invention as fuel composition or fuel additives in the fuel compositions. The fuel composition can be gasoline, diesel, naphtha or jet fuel.

A further object of the invention is to provide a fuel composition comprising hydrocarbon components produced by subjecting a terpene feed and a hydrogen gas to a hydrodesulphurization step in the presence of a hydrodesulphurization catalyst.

A still further object of the invention is to provide an additive to be used in a fuel composition comprising hydrocarbon components produced by subjecting a terpene feed and a hydrogen gas to a hydrodesulphurization step in the presence of a hydrodesulphurization catalyst.

DETAILED DESCRIPTION OF THE INVENTION

Figure 1:
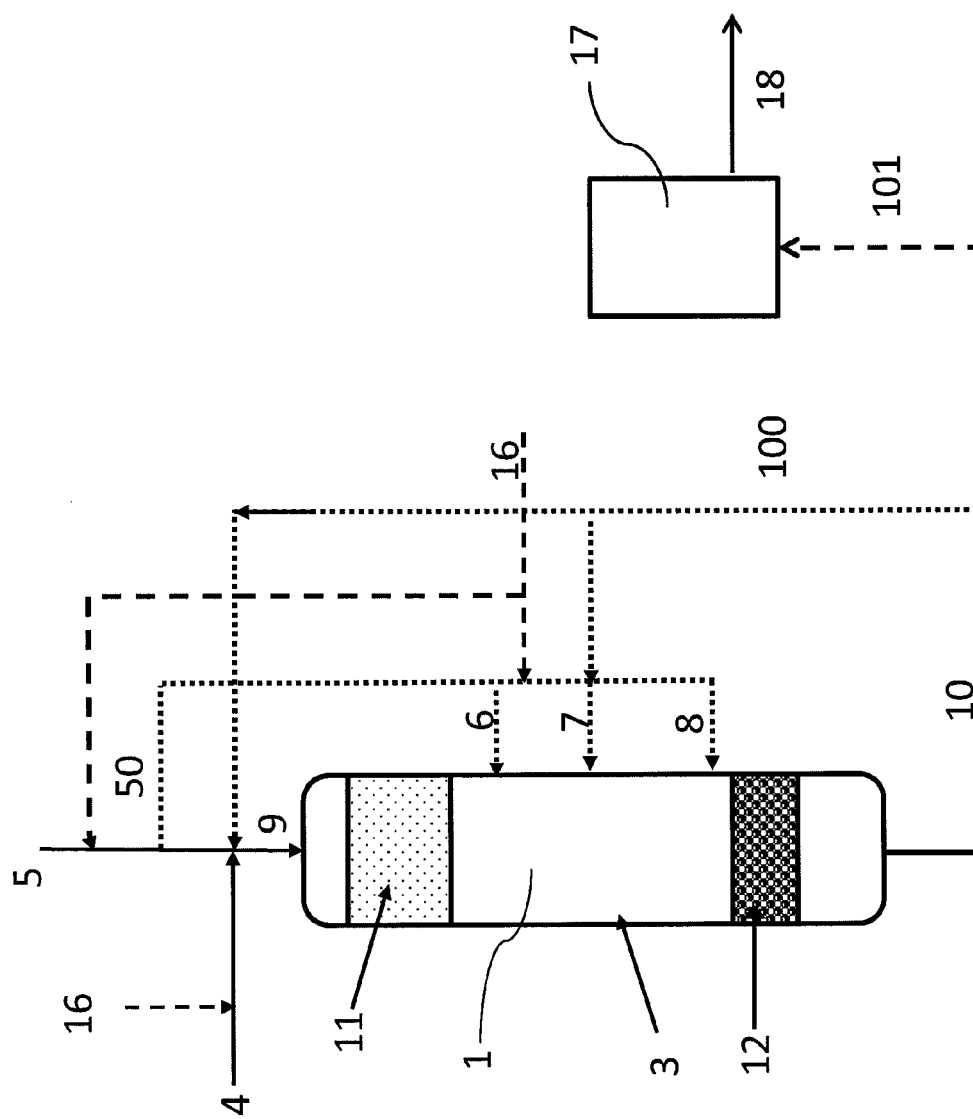
FIG. 1 shows an embodiment of an apparatus of the invention comprising one hydrogenation reactor where a hydrodesulphurization catalyst is packed in one layer in the reactor.

An object of the invention is to provide a process for producing hydrocarbon components, comprising:
providing a terpene feed;
subjecting the terpene feed and a hydrogen gas feed to a hydrogenation step in the presence of a hydrodesulphurization catalyst to produce hydrocarbon components.

Terpenes constituting the starting material for the process of the present invention can be obtained from any suitable source. The hydrocarbons can contain heteroatoms and minor amounts of heavier hydrocarbons as a contaminant. In an embodiment of the invention, the terpene feed is composed of $C_{10}H_{16}$ terpenes. In another embodiment of the invention, the terpene feed is substantially composed of crude turpentine. In the present invention, the term 'crude turpentine' is to be understood to include crude turpentine of wood origin. Crude turpentine from any source of this origin is suitable for the purpose of the invention. In an embodiment of the invention, the crude turpentine is obtained from kraft pulping process of coniferous wood as crude sulphate turpentine which is predominantly composed of volatile unsaturated $C_{10}H_{16}$ terpene isomers derived from pitch. The crude turpentine of this origin is also referred to as crude sulphate turpentine (CST). Due to the process chemicals used in kraft process, sulphur is included the crude turpentine as a contaminant, amounting typically up to 6% by weight.

In another embodiment of the invention, the crude turpentine is derived from mechanical pulping of wood, like from grinding and pressure grinding, thermomechanical pulping, or chemimechanical pulping. From these processes, turpentine can be retrieved in gaseous form, provided that the process is equipped with gas collecting means. Also from chipping of wood or saw mills turpentine can be recovered in gaseous form.

In a further embodiment, crude turpentine is meant to include distillation bottoms from turpentine distillation.

In a still further embodiment, crude turpentine is meant to include turpentine separated from crude tall oil which is retrieved from kraft pulping process of coniferous trees.

In a still further embodiment, crude turpentine is meant to include one or more volatile unsaturated terpenes, especially α-pinene, β-pinene and Δ-3-carene, which is/are isolated from turpentine or any other source.

The crude turpentine can be used in purified or unpurified form.

In a further embodiment of the invention, also a mixture of various crude turpentines can be used as a terpene feed.

In another embodiment of the invention, sulphur-containing C5 to C10 hydrocarbon streams from wood processing industry or side streams from wood processing industry can be used as a terpene feed.

The hydrogenation step in the process can be accomplished by using a conventional hydrodesulphurization (HDS) catalyst known in the art. It is to be noted that any catalysts conventionally used for removal of heteroatoms from the organic compounds can be used in the process of the invention. Heteroatoms are typically sulphur, oxygen and nitrogen. Particularly, catalysts which are typically referred to as (HDO) catalysts in the art can be used in the process. HDO hydrodeoxygenation catalysts are especially intended for oxygen removal but are usable for sulphur and nitrogen removal as well. In the present invention, the HDS catalyst is selected from a group consisting of $NiO/MoO_3$, $CoO/MoO_3$ and a mixture of $NiO/MoO_3$ and $CoO/MoO_3$ on a support selected from $Al_2O_3$ and $Al_2O_3$—$SiO_2$. In a specific embodiment of the invention, $NiO/MoO_3$ on the $Al_2O_3$ support is used.

In the following, the invention will be further illustrated in light of the crude sulphate turpentine (CST) as a starting material, while it is to be understood that the invention is not limited to this embodiment.

The HDS catalyst used in the present invention has a capability of hydrogenating the olefinic bonds of the terpene compounds included in CST. Moreover, compounds having bicyclic terpene structure are decomposed and at least one of the bicyclic rings is opened. In addition, the HDS catalyst is advantageously capable of simultaneously removing undesirable sulphur compounds present in the CST, like dimethyl sulphide, dimethyl disulphide and methyl mercaptane, by converting the organic sulphur compounds to gaseous hydrogen sulphide. Sulphur removal is generally called hydrodesulphurization (HDS). Thus, in the present invention, CST undergoes a HDS step in which the above chemical transformation reactions are simultaneously taken place.

In the HDS step, light gaseous hydrocarbons, like methane, are also formed. Generally, gaseous compounds including hydrogen sulphide, methane and $H_2$ formed in the HDS step can be easily discarded from the process and separated from each other, if desired.

It is characteristic of the HDS catalyst that sulphur has to be present to maintain the catalytic activity of the catalyst. Advantageously, when the hydrocarbon feed comprises CST, hydrogen disulphide needed for catalytic activity of the catalyst is thus simultaneously provided from the sulphur compounds inherently present in CST. Gaseous hydrogen sulphide can be easily discarded from the mixture of the gasoline components, if necessary.

It may be necessary to supply supplementary sulphur to the process to maintain the catalytic activity of the catalyst. Supplementary sulphur can be supplied in gaseous form like hydrogen sulphide, or it can be any material that produces hydrogen sulphide in the process, like organic sulphur compounds, such as dimethyl disulphide. In an embodiment of the invention, supplementary sulphur is provided by recirculating the $H_2S$-containing gas retrieved from the mixture of fuel components produced by the process of the invention. The amount of supplementary sulphur depends on the amount of sulphur in the CST. Generally, the $H_2$ feed/$H_2S$ relation must be maintained over about 0.0001. This means that an added amount of sulphur is in the range of about 100 to about 200 ppm. Sulphur can be fed to the initial crude turpentine feed, for example, or to the hydrogenation step.

The amount of hydrogen gas needed to hydrogenate the olefinic bonds of the terpene structure is determined by the amount of the turpentine feed. A suitable amount of hydrogen can be determined by a man having ordinary skills in the art. Typically, the relation $H_2$ feed/turpentine feed is in the range of about 100 to about 1500 Nl/l, preferably about 100 to about 350, more preferably about 100 to about 300 (Nl=normal liter).

If desired, any hydrocarbon component can be isolated from the mixture of the hydrocarbon components received in the process of the invention.

In an embodiment of the invention, the mixture of hydrodesulphurized hydrocarbon components is subjected to a hydrogen sulphide removal step to remove any residual hydrogen sulphide from the mixture.

Terpenic compounds present in the CST undergo a number of chemical reactions including hydrogenation, isomerization, dehydrogenation, hydrogenolysis and C—C bond cleavage. Favour of the various reactions is influenced by the reactions conditions, especially temperature and feeding speed (WHSV) of the CST to the reaction. Various reactions of the initial components of the CST, i.e. α-pinene and Δ-3-carene, can be described, for example, as follows:

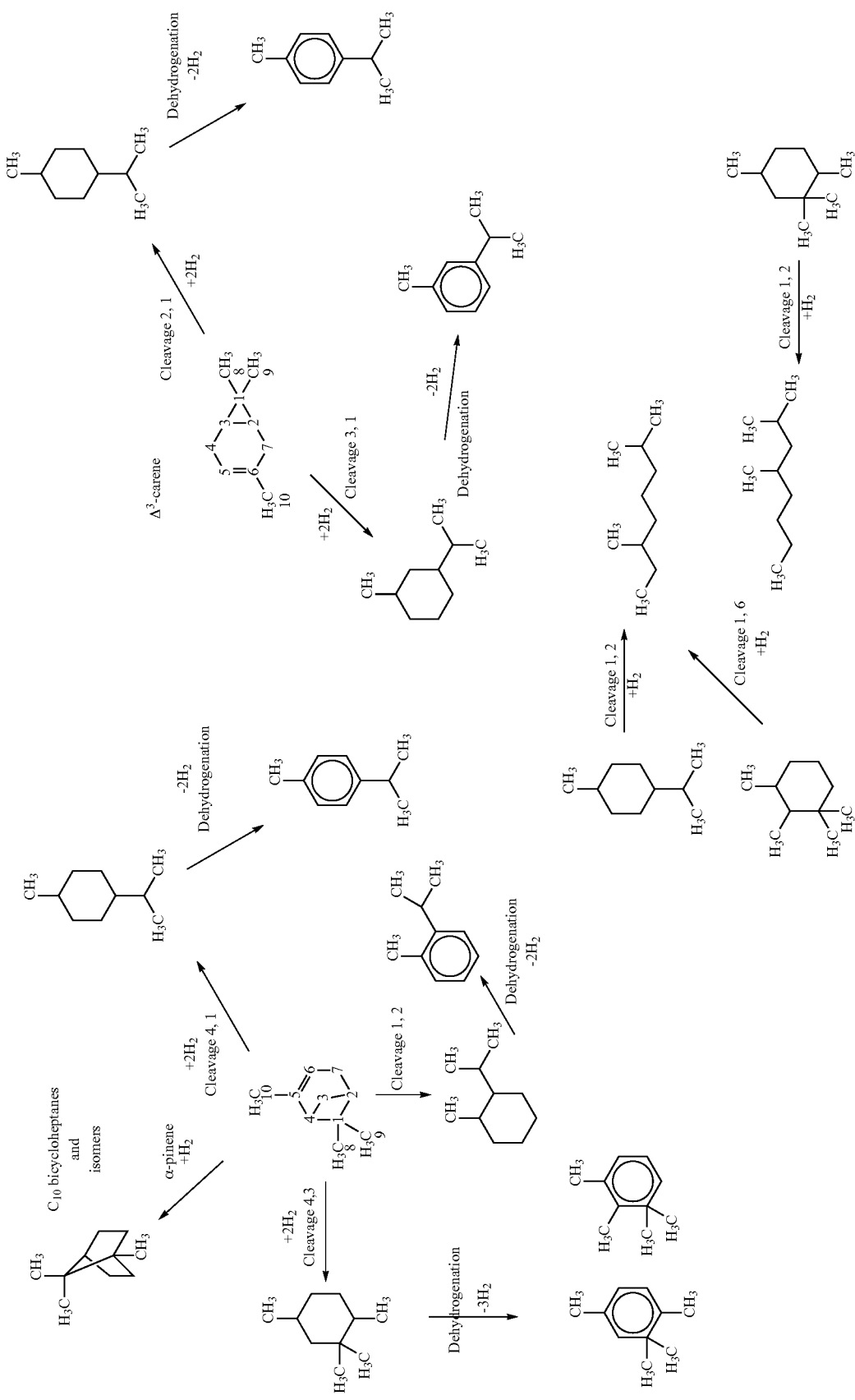

Compounds obtained in the process of the invention can be classified in unsaturated non-terpenic hydrocarbons, terpenes, acyclic, polycyclic, monocyclic and aromatic hydrocarbons. The main components obtained in the process of the invention are the following compounds and their isomers:

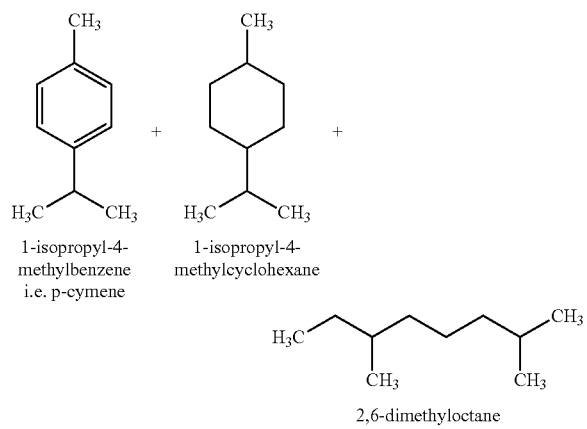

1-isopropyl-4-methylbenzene i.e. p-cymene 1-isopropyl-4-methylcyclohexane 2,6-dimethyloctane If no ring opening takes place completely in the HDS step, bicyclic C10 compounds can also be formed, the structure of which corresponds to that of the starting compounds except that the olefinic bonds are reduced. It has been recognized that when operating at lower temperatures, ring opening of the initial compounds is reduced and the relative amount of the bicyclic compounds is increased. The temperature in the HDS step can vary from about 200 to about 450° C., preferably from about 275° C. to about 425° C. The most preferable operating temperature is about 400° C. When operating at temperatures over about 330° C., there is a tendency that the content of the aromatic hydrocarbons, especially 1-propyl-4-methylbenzene, also called cymene or p-cymene, is increased. This effect has a benefit that the octane number of the product is increased and the content of the bicyclic compounds are reduced, respectively. The octane number of the product can thus be controlled by means of process conditions. If desired, an octane enhancer such as ethanol can be added to the product obtained by the process of the invention.

The proportions of the various hydrocarbon components produced in the process can be influenced by controlling the temperature and/or WHSV through the catalyst layer. For example, the HDS step can be carried out by using a gradient temperature where the temperature of the catalyst layer in the inlet arranged for terpene feed is higher than the temperature of the catalyst layer in the outlet for product recovery. By controlling the temperature and/or WHSV in the HDS step, the content of the aromatics predominantly composed of cymenes, particularly p-cymene, in the reaction mixture can be raised up to 50%. In this embodiment, the temperature in the HDS step ranges from about 330° C. to about 425° C.

Recirculation of the product produced in the hydrogenation step also provides means for affecting the proportions of the hydrocarbon components in the mixture. Especially, recirculation has an advantage that the content of aromatics, particularly p-cymene, can be increased at lower temperatures.

Hydrodesulphurization of the CST is highly exothermic reaction in which temperature can rise to a level which is detrimental to the catalytic activity of the catalyst and/or product quality. In some cases, it may be necessary to control the temperature variations. Recirculation of the product, i.e. the mixture of the hydrocarbon components, provides an efficient means for constraining the exothermic reaction whereby the recycled product stream acts as an inert media lowering the temperature of the bed in a controlled manner. In an embodiment of the invention, the hydrocarbon components obtained in the process are circulated back to the initial turpentine feed and/or to the ongoing HDS step.

The pressure in the HDS step can vary from about 10 to about 150 bar, preferably from about 20 to about 70 bar. More preferably, the process of the invention is performed at a pressure of about 25 to about 50 bar.

The HDS step can be effected either in a single catalyst layer or in two or more catalyst layers. The one or more catalyst layers can be arranged in a single reactor or in several reactors as described in more detail below.

After the HDS step, the sulphur is retrieved in the form of gaseous hydrogen sulphide which easily evaporates from the product. The sulphur content of the product mixture can be reduced to a level of 10 ppm at most, the level being within the range stipulated for gasoline fuels. However, in some cases it may be necessary to remove the residual hydrogen sulphide from the product received in the HDS step in order to achieve the above sulphur level. This can be accomplished by various methods, like stripping, flashing or bubbling with inert gas, for example nitrogen gas. If desired, hydrogen sulphide retrieved can be led to the hydrogenation step for maintaining the catalytic activity of the catalyst.

Moreover, if appropriate, a pre-treatment step can be accomplished prior to the HDS step. The pre-treatment step can include one or several of the following procedures: distillation, filtration and cleaning of the CST.

The process of the invention produces a mixture of hydrocarbon components. In order to be able to utilize the obtained hydrocarbon mixture in an optimum manner, the mixture is further subjected to separation to separate the mixture into various fuel grade hydrocarbon fractions. Separation can be realized conveniently by distillation. Specifically, product streams having distillation curves conforming to those of standardized diesel, gasoline, naphtha and jet fuels are achieved. As a general, hydrocarbons distilling at a temperate range from 180 to 370° C. are obtained as a middle distillate conforming to diesel fuel quality standard EN 590. Hydrocarbons distilling at temperatures ranging from 150° C. to 210° C. are useful as high quality gasoline fuel. They conform to the standard EN 228. Hydrocarbons having a distillation temperature between 160° C. and 300° C. are useful as aviation applications, generally referred to as jet fuel. The jet fuel conforms to standard ASTM D-1655. Hydrocarbons having a distillation temperature above 370° C. is useful as heavy fuel oil. The composition of the products obtained with the process of the present invention depends on the feed material used as well as on the operation conditions of the process.

The process of the invention provides high quality hydrocarbon components that are useful as fuel or as a fuel additive in the conventional fuel compositions. The invention thus further provides a use of the hydrocarbon components prepared by the process of the invention as a fuel composition or as an additive in the fuel compositions. The fuel composition can be gasoline, diesel, naphtha or jet fuel. The properties of fuel composition conform to those of the desired standards, especially to EN590, EN228 and ASTM D1655. Preferably, the process of the invention produces hydrocarbon components suitable as gasoline fuel.

Another object of the invention is to provide an apparatus for producing hydrocarbon components. The apparatus of the invention is adapted to realize an embodiment of the process of the invention. The apparatus comprising at least one hydrogenation reactor 1, 1' comprising at least one catalyst layer 3, 3' of a HDS catalyst
terpene inlet pipe 9
hydrogen feed pipe 5, 50, 50'
product outlet pipe 10, 15 for recovering a mixture of the hydrocarbon components.

A further object of the invention is to provide a fuel composition comprising hydrocarbon components produced by subjecting a terpene feed and a hydrogen gas to a hydrodesulphurization step in the presence of a hydrodesulphurization catalyst.

A still further object of the invention is to provide an additive to be used in a fuel composition comprising hydrocarbon components produced by subjecting a terpene feed and a hydrogen gas to a hydrodesulphurization step in the presence of a hydrodesulphurization catalyst.

With reference to FIG. 1, crude sulphate turpentine and $H_2$ are fed to a hydrogenation reactor 1 including a catalyst layer 3 for hydrodesulphurization of the CST. The hydrogenation reactor is for example in a form of a separate tank or a tubular reactor. CST and $H_2$ are supplied via terpene feed pipe 4 and hydrogen feed pipe 5, respectively. In the FIG. 1, CST and $H_2$ feeds are combined and fed together via terpene inlet pipe 9 to the reactor 1. In an embodiment of the invention, inlet pipe 9 is omitted and the feed pipes 4 and 5 enter separately the reactor 1.

The catalyst bed comprising a HDS catalyst can be packed in one or more layers 3, 3' in the reactor 1. Also, one or more of the catalyst layers can be diluted with an appropriate medium. The diluting material can be for example the passive material used in passive layers described below, or another catalyst suitable for hydrogenation. In an embodiment, where several catalyst layers are used in the reactor, the first layer downstream of the turpentine feed is diluted while the remaining layers are undiluted. If the first layer downstream of the turpentine feed is diluted, it acts as a pre-hydrogenation catalyst. In FIG. 1, the HDS catalyst is packed in one layer 3. Preferably, the catalyst layer 3 is undiluted in the embodiment illustrated in FIG. 1.

$H_2$ feed can be supplied to reactor 1 downstream to the turpentine feed. $H_2$ feed can also be supplied to reactor 1 via $H_2$ feed pipe 50 at one or more locations between the terpene inlet pipe 9 and the product outlet pipe 10, preferably at one or more locations in the catalyst layer 3, to control reaction conditions of the exothermic hydrogenation reaction. These $H_2$ feed inlets are denoted by reference numbers 6, 7 and 8.

$H_2$ can also be fed upstream to the turpentine feed, i.e. the $H_2$ and turpentine feeds are countercurrent to each other (not shown in FIG. 1).

Catalytic hydrodesulphurization reaction and other reactions, i.e. ring opening and saturation of olefinic bonds, are carried out in a catalyst layer 3 packed in the reactor 1. Product is recovered from the reactor 1 via product outlet pipe 10. At least a portion of the product, i.e. a mixture of the hydrocarbon components, can be circulated back to the reactor 1 through recirculation pipe 100 as shown by the dotted line in the Figure. In the recirculation, the product can be combined with the initial CST and $H_2$ feeds into a single feed flow and supplied to the reactor 1 through the terpene inlet pipe 9 as shown in the Figure. The recirculation pipe 100 can also be arranged to the reactor 1 separately from the terpene inlet pipe 9. The product can also be supplied to the reactor 1 at one or more locations between the terpene inlet pipe 9 and the product outlet pipe 10, preferably at one or more locations in the catalyst layer 3 via inlets 6, 7 and 8.

Moreover, at least a portion of the product can be supplied via pipe 101 to a separating reactor 17 for separating one or more hydrocarbon fractions from the mixture of the hydrocarbon components. The reactor 17 is appropriately a distillation apparatus in which the hydrocarbon fractions are separated based on differences in boiling points. One or more of the isolated fractions useful as various fuel grade components can be recovered via pipe 18.

Also, passive layers 11 and 12 comprising suitable passive or inert material, such as $Al_2O_3$, SiC or glass beads can be arranged in the reactor 1. Their task is to act as guard beds against harmful substances in the feed. When a passive layer is arranged in the reactor as the first layer to receive the feed via inlet pipe 9, upstream of the catalyst layer, it acts also as preheating and cleaning layer for the feed. It also enhances the even distribution of the feed to the catalyst. In FIG. 1, a first passive layer 11 is arranged upstream of the catalyst layer 3, and a second passive layer 12 is arranged downstream of the catalyst layer 3.

If appropriate, supplementary sulphur from an outer source is supplied via sulphur feed pipe 16 to the reactor 1 through inlets 6, 7, 8, and/or 9. Supplementary sulphur can also be fed to the turpentine feed. Supplementary sulphur fed via pipe 16 can be any compound that produces hydrogen sulphide in the process, like organic sulphur compounds, such as dimethyl disulphide.

The crude turpentine is pumped to the reactor 1 at a desired speed. Feed rate WHSV (weight hourly spatial velocity) of the turpentine feed is proportional to an amount of the catalyst and is calculated according to the following equation:

$$WHSV[h^{-1}] = \frac{V_{feed[g/h]}}{m_{catalyst[g]}}$$

wherein $V_{feed[g/h]}$ means a pumping velocity of the crude turpentine feed, and $m_{catalyst[g]}$ means an amount of the catalyst;

WHSV is typically in the range from about 0.5 to about 10, preferably in the range of about 1 to about 5.5.

The proportions of the hydrocarbon components in the product mixture produced by the process can be influenced by adjusting WHSV to a desirable range. In an embodiment of the invention, WHSV is adjusted to the range from about 2 to about 3.5 where a production of p-cymene is increased.

The amount of hydrogen feed is proportional to the amount of the turpentine feed. Typically, the relation $H_2$ feed/turpentine feed is in the range of about 100 to about 1 500 Nl/l, for example about 100 to about 350 Nl/l (Nl=normal liter).

Figure 2:
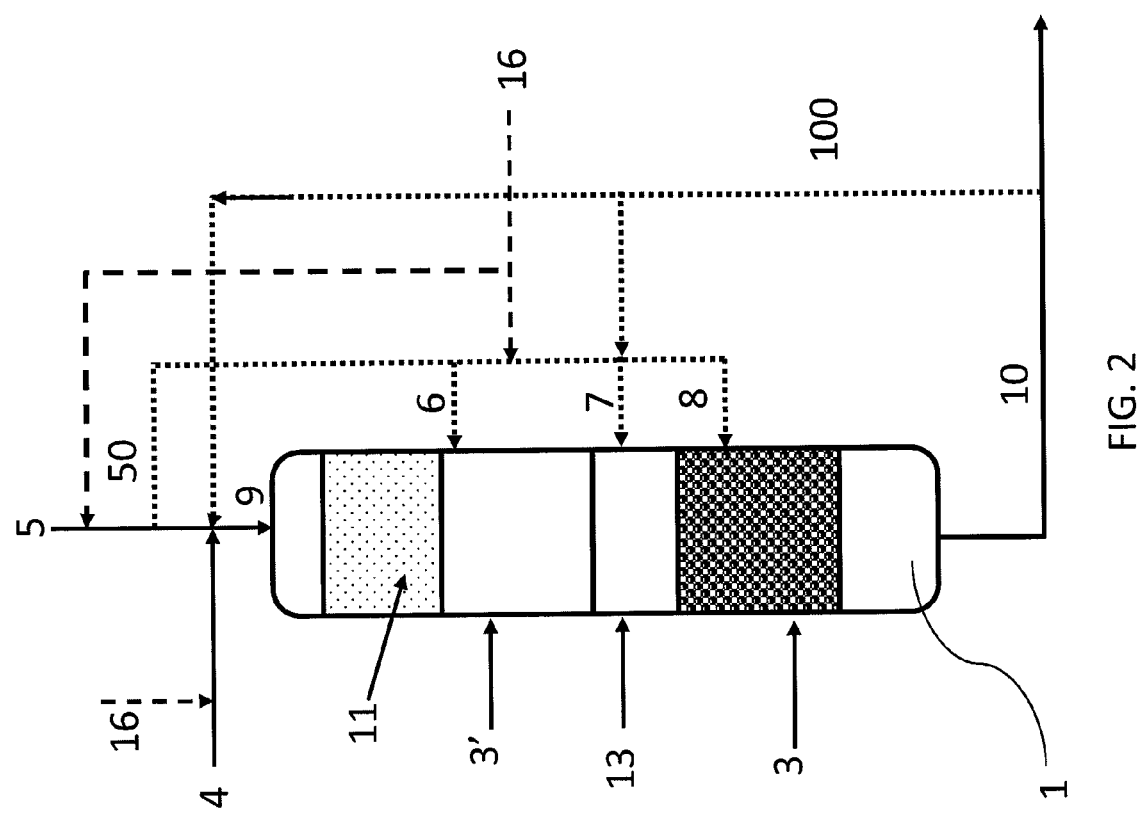
FIG. 2 shows another embodiment of an apparatus of the invention comprising one hydrogenation reactor where a hydrodesulphurization catalyst is packed in two separate layers in the reactor.

FIG. 2 shows another embodiment of an apparatus of the invention where a HDS catalyst is packed in two separate catalyst layers, a first catalyst layer 3' and a second catalyst layer 3, in a hydrogenation reactor 1. The first catalyst layer 3' is arranged upstream of the second catalyst layer 3 and it comprises diluted hydrogenation catalyst material. The second catalyst layer 3 comprises undiluted hydrogenation catalyst material. Further, an intermediate insulating layer 13 is disposed between the two catalyst layers to prevent the layers to mix with each other and to facilitate the operating of the first and second catalyst layers in different temperatures. As an intermediate layer the same material can be used as in the passive layers. A passive layer 11 is arranged upstream of the first catalyst layer 3'. The H₂ feed can be supplied to the reactor 1 either downstream to the turpentine feed, or the H₂ feed can be supplied to the reactor 1 via H₂ feed pipe 50 at one or more locations denoted by reference numbers 6, 7 and 8. When appropriate, the H₂ feed can be divided so that a part of the H₂ feed is supplied to the first catalyst layer 3' and a part of it is supplied to the second catalyst layer 3, as shown in FIG. 2.

As in an embodiment illustrated in FIG. 1, external sulphur can be supplied via sulphur feed pipe 16 to the reactor 1, if appropriate. Also, external sulphur feed can be divided so that a part of the external sulphur feed is supplied to the first catalyst layer 3' and a part of it is supplied to the second catalyst layer 3.

In an embodiment of the invention, when NiMo/Al₂O₃ or CoMo/Al₂O₃ catalysts are being used in the catalyst layer 3 and/or 3' for accomplishing the hydrogenation step, the catalyst has to be activated before it is effective in hydrogenation. The activation comprises several steps, of which one is treating the catalyst with activating sulphur compound, for example dimethyl disulphide. The activation of such catalysts is common knowledge in the art and will thus not be discussed here in detail.

Product recovered via product outlet pipe 10 can be further led to a separating reactor 17 in a similar manner as shown in FIG. 1 (not shown in FIG. 2).

Figure 3:
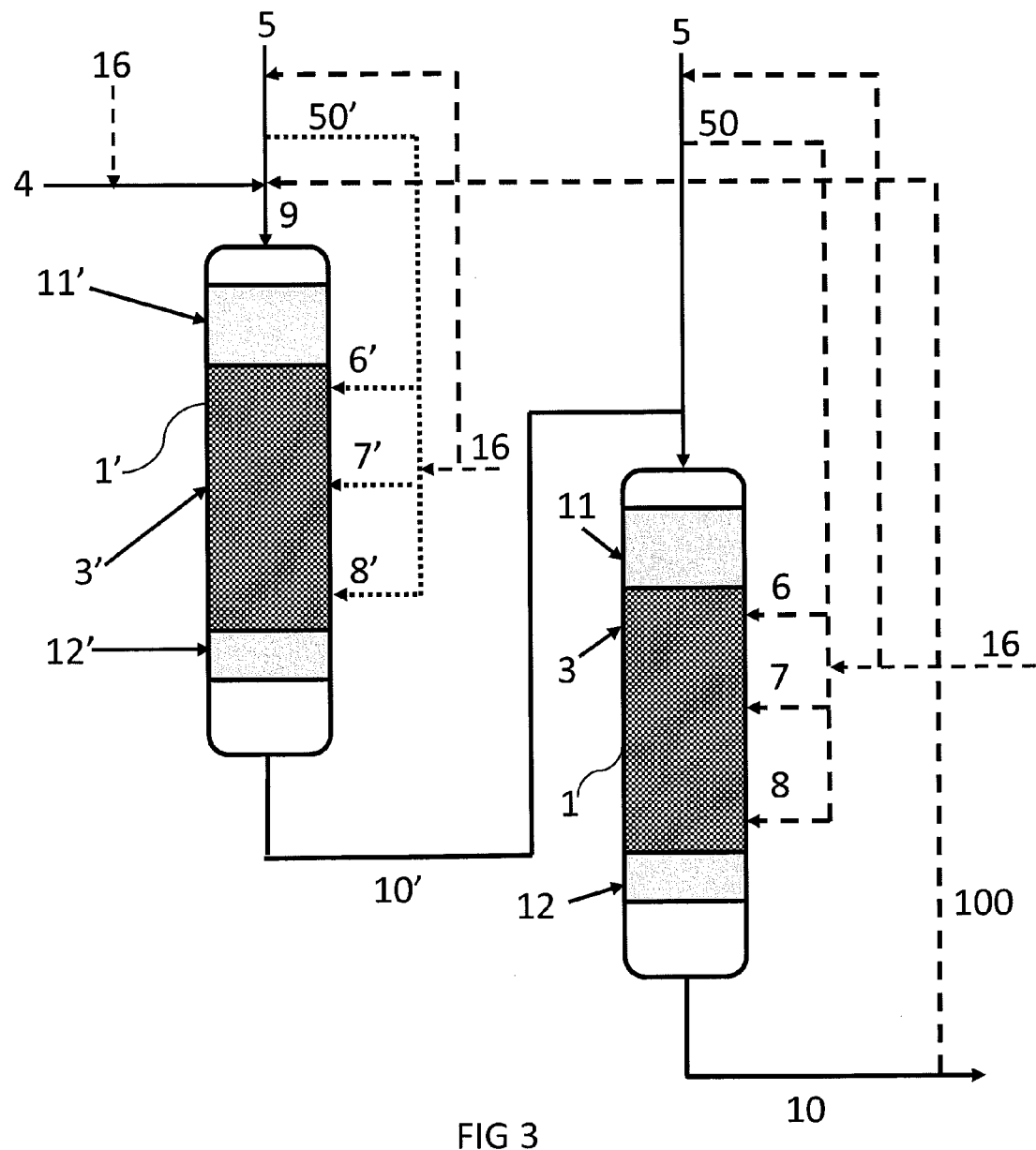
FIG. 3 shows an embodiment of an apparatus of the invention comprising two hydrogenation reactors where a hydrodesulphurization catalyst is packed in one layer in each reactor.

FIG. 3 shows an embodiment of the invention, where a HDS catalyst is packed in two separate catalyst layers, a first catalyst layer 3' and a second catalyst layer 3, which layers 3' and 3 are disposed in separate reactors, a first reactor 1' and a second reactor 1, respectively. The first reactor 1' is arranged upstream of the second reactor 1. In an embodiment of the invention, the first catalyst layer 3' includes diluted HDS catalyst, whereas the second catalyst layer 3 includes undiluted HDS catalyst. Passive layers 11' and 12', and 11 and 12 are arranged in the reactors 1' and 1, respectively.

Crude sulphate turpentine is fed to the first reactor 1'. The product obtained from the first reactor 1' is recovered via pipe 10' and further supplied to the second reactor 1. The product is recovered via product outlet pipe 10 from the second reactor 1.

H₂ feed is supplied to both reactors 1' and 1. H₂ feed can be supplied either downstream to the turpentine feed, or the H₂ feed can be supplied to the reactors 1' and 1 via H₂ feed pipes 50' and 50, at one or more locations denoted by reference numbers 6', 7' and 8', and 6, 7 and 8, respectively.

In another embodiment of the invention, both first and second catalyst layers 3' and 3 comprise diluted hydrogenation catalyst material. The catalyst layers may be arranged in the same reactor, as in the embodiment shown in FIG. 2, or they may be arranged in separate reactors, as illustrated in the embodiment shown in FIG. 3.

In an embodiment of the invention, both first and second catalyst layers 3', 3 comprise the same catalyst material, either NiMo/Al₂O₃ or CoMo/Al₂O₃. In another embodiment of the invention, the catalyst layers comprise different catalyst materials, preferably the first catalyst layer 3' comprises NiMo/Al₂O₃ and the second catalyst layer 3 comprises CoMo/Al₂O₃.

At least a portion of the product, i.e. a mixture of the hydrocarbon components, can be circulated back to the first reactor 1' through recirculation pipe 100 as shown by the dotted line in the FIG. 3. In the recirculation, the product can be combined with the initial CST and H₂ feeds into a single feed flow and supplied to the reactor 1' through the terpene inlet pipe 9 as shown in the Figure. The recirculation pipe 100 can also be arranged to the reactor 1' separately from the terpene inlet pipe 9. The product can also be supplied to the reactor 1' at one or more locations between the terpene inlet pipe 9 and the pipe 10', preferably at one or more locations in the catalyst layer 3' via inlets 6', 7' and 8'.

If appropriate, external sulphur is supplied via sulphur feed pipe 16 to the reactor 1' through inlets 6', 7', 8' and/or 9, and/or to the reactor 1 through inlets 6, 7 and/or 8. Supplementary sulphur can also be fed to the turpentine feed.

Product recovered via product outlet pipe 10 can be further led to a separating reactor 17 in a similar manner as shown in FIG. 1 (not shown in FIG. 3).

Figure 4:
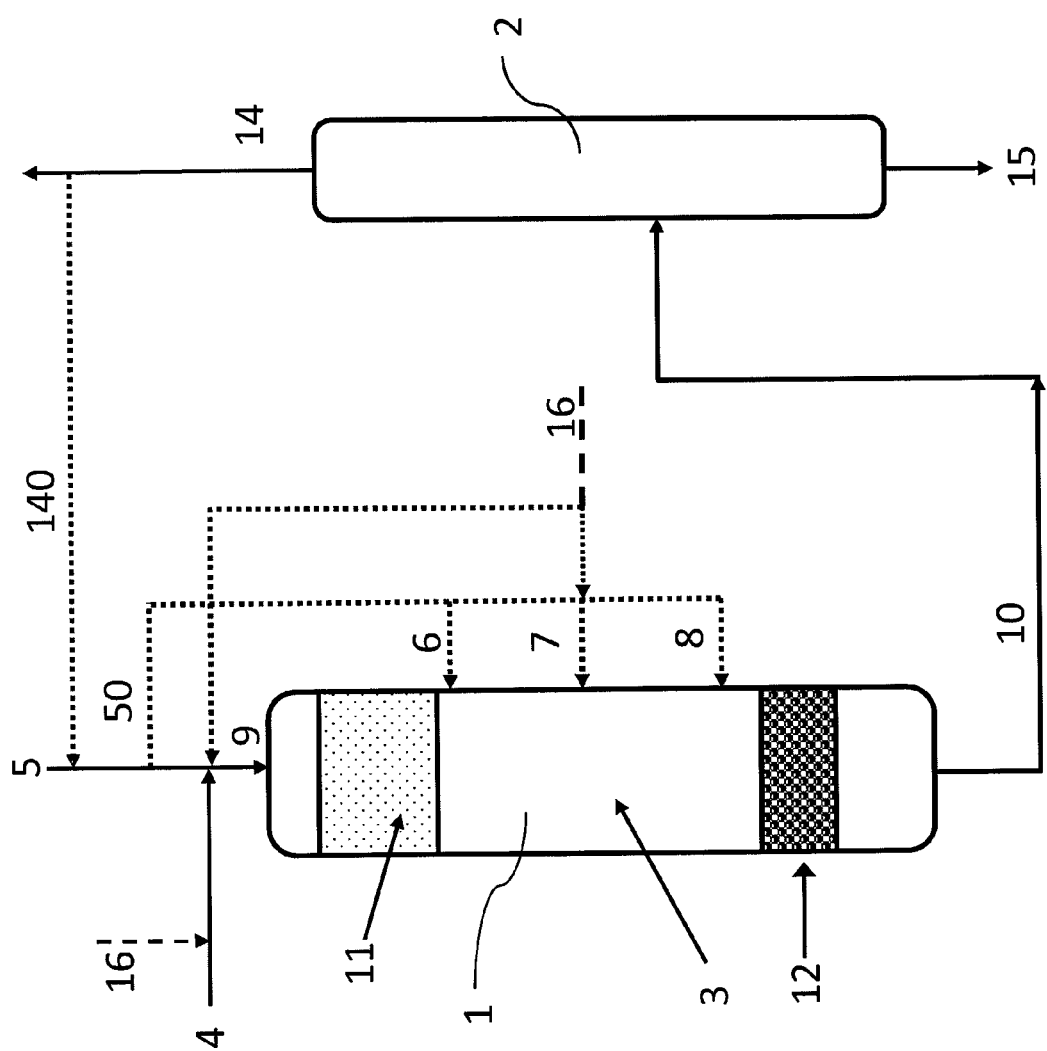
FIG. 4 shows an embodiment of an apparatus of the invention comprising a hydrogenation reactor and a hydrogen sulphide separator.

FIG. 4 shows an embodiment of the apparatus of the invention, where the product recovered from the catalytic hydrodesulphurization reaction of the CST in a liquid form is fed from the hydrogenation reactor 1 via pipe 10 to a H₂S removal reactor 2. In the H₂S removal reactor 2, gaseous compounds composing predominantly of hydrogen sulphide, hydrogen and methane are removed from the product via pipe 14. This can be accomplished for example by stripping, flashing or bubbling with inert gas, such as nitrogen.

When supplementary sulphur supply is desired, at least part of the gaseous compounds recovered from the reactor 2 can be recirculated back to the reactor 1 via H₂S recirculation pipe 140 as shown in FIG. 4 by a dotted line. Supplementary sulphur can also be supplied to the reactor 1 from an outer source via sulphur feed pipe 16 through inlets 6, 7, 8, and/or 9. Supplementary sulphur can also be fed to the turpentine feed. Supplementary sulphur fed via pipe 16 can be any compound that produces hydrogen sulphide in the process, like organic sulphur compounds, such as dimethyl disulphide.

The fuel grade product that has been treated in the H₂S removal reactor 2 is recovered via product outlet pipe 15. As in the embodiment illustrated in the FIG. 1, at least a portion of the product can be supplied to a separating reactor 17 for separating one or more hydrocarbon fractions from the mixture of the hydrocarbon components. Also, recirculation of the product obtained in the process of the invention via product recirculation pipe 100 can be accomplished in a similar manner as in FIG. 1 in an embodiment illustrated in FIG. 4 (not shown).

Gaseous compounds can also be led to a gas treatment system (not shown in FIG. 4). In the gas treatment system, gaseous compounds recovered from the H₂S reactor are treated. Unreacted hydrogen is cleaned from hydrogen sulphide and methane by means of membrane technique, for example. The cleaned hydrogen is pressurized and can be recycled into the reactor 1 (not shown). Hydrogen sulphide and methane are utilized e.g. as energy by burning. Hydrogen sulphide can also be recycled to pulp mills chemical recovery cycle and converted to elementary sulphur by Claus process.

The following examples are presented for further illustration of the invention without limiting the invention thereto.

Example 1

Crude turpentine obtained from kraft pulping process, i.e. CST, was used as a crude turpentine feed. The crude turpentine comprised 50-60% α-pinene, 20-30% of Δ-carene, the rest being other terpenes. The sulphur content was about 1.5%.

TABLE 1

| Feed | CST |
|---|---|
| Sulphur content (%) | about 1.5 |
| Pumping of feed ($V_{feed}$) (g/h) | 10 |
| Catalyst | NiMo/Al$_2$O$_3$ |
| Amount of catalyst (g) | 10 |
| Reaction pressure (bar) | 50 |
| H$_2$ (l/h) | 15 |
| WHSV (h$^{-1}$) | about 1 |
| Temperature of bed (° C.) | 300 |
| H$_2$ feed/turpentine feed (Nl/l) | 1250 |

The catalyst was packed into one layer in the reactor.

The composition of the product obtained was measured for two samples. For the first sample, no hydrogen sulphide was removed from the product sample. This is denoted by sample number 1 in Table 2 below. For the second sample, hydrogen sulphide was removed from the product sample by bubbling it with gas. This is denoted by sample number 2. The results from the two analyses are summarized in Table 2.

TABLE 2

| | Sample number | |
|---|---|---|
| | 1 | 2 |
| Sulphur (ppm) | 60 | 10 |
| Density at 15° C. (g/mL) | 0.8124 | 0.8124 |
| Vapour pressure (DVPE) | <1 | <1 |
| MON | 75 | 75 |
| RON | 75 | 75 |
| Benzene content | <0.1 | <0.1 |
| Oxidation stability | >720 | >720 |
| Hydrocarbon type content | | |
| Olefins | 3.2 | 3.2 |
| Aromatics | 13.6 | 13.6 |
| Unsaturated hydrocarbons (non terpenes) | n.d. | n.d. |
| Terpenes (%) | n.d. | n.d. |
| Acyclic hydrocarbons (%) | 14 | 14 |
| Polycyclic hydrocarbons (%) | 16 | 16 |
| Monocyclic hydrocarbons (%) | 52 | 52 |
| Aromatic hydrocarbons (%) | 15 | 15 |
| Others (%) | 3 | 3 | n.d.: not detected
MON = Motor Octane Number
RON = Research Octane Number

The results indicate that the terpene structure is decomposed and the olefinic bonds are hydrogenated so as to provide components that are suitable for use as gasoline components.

Example 2

The same turpentine feed as in Example 1 was used in this Example. The process parameters are summarized in Table 3 below. The catalyst was packed in two layers in the reactor. The first layer comprised of diluted catalyst and the second layer comprised of undiluted catalyst. The diluted catalyst layer comprised of 40% catalyst and 60% of SiC, calculated on volume basis.

TABLE 3

| Feed | CST |
|---|---|
| Sulphur content (%) | about 1.5 |
| Pumping of feed ($V_{feed}$) (g/h) | 40 |
| Catalyst | NiMo/Al$_2$O$_3$ |
| Amount of catalyst (g) | 30 (10 g diluted + 20 g undiluted) |
| Reaction pressure (bar) | 50 |
| H$_2$ (l/h) | 30 |
| WHSV (h$^{-1}$) | about 1.3 |
| Temperature of bed (° C.) | 340 |
| H$_2$ feed/turpentine feed (Nl/l) | 640 |

As in Example 1, the composition of the product obtained was measured for two samples. The sample numbers have the same meanings as in Example 1.

TABLE 4

| | Sample number | |
|---|---|---|
| | 1 | 2 |
| Sulphur (ppm) | 60 | 6 |
| Density at 15° C. (g/mL) | 0.8202 | 0.8202 |
| Vapour pressure (DVPE) | <1 | <1 |
| MON | 87 | 87 |
| RON | 96 | 96 |
| Benzene content | <0.1 | <0.1 |
| Oxidation stability | >1576 | >1576 |
| Hydrocarbon type content | | |
| Olefins | 1.7 | 1.7 |
| Aromatics | 28.6 | 28.6 |
| Unsaturated hydrocarbons (non terpenes) | n.d. | n.d. |
| Terpenes (%) | n.d. | n.d. |
| Acyclic hydrocarbons (%) | 10 | 10 |
| Polycyclic hydrocarbons (%) | 10 | 10 |
| Monocyclic hydrocarbons (%) | 40 | 40 |
| Aromatic hydrocarbons (%) | 30 | 30 |
| Others (%) | 10 | 10 |

The quantities in both of the examples were measured in accordance with the following standards:
Sulphur: EN ISO 20846
Density at 15° C. (g/mL): EN ISO 12185
Vapour pressure (DVPE): EN 13016-1
Benzene content: EN 238
Oxidation stability: EN ISO 7536
Hydrocarbon type content: EN 15553

The test results clearly show that it is possible to influence on the shares of product components. By increasing the content of the aromatic compounds one can increase the octane number of the gasoline components produced from CST.

Example 3

The products obtained in Examples 1 and 2, from which hydrogen sulphide was removed by bubbling with inert gas, were blended with a standard 95E gasoline in various mixing ratios. The mixing ratios were as follows:
Sample 1: 95E gasoline blended with 5% of sample number 2 of Example 1.
Sample 2: 95E gasoline blended with 10% of sample number 2 of Example 1.
Sample 3: 95E gasoline blended with 5% of sample number 2 of Example 2.
Sample 4: 95E gasoline blended with 10% of sample number 2 of Example 2.

TABLE 5

| | 95E gasoline | Sample 1 | Sample 2 | Sample 3 | Sample 4 |
|---|---|---|---|---|---|
| MON | 85.4 | 85.3 | 84.9 | 85.2 | 85.0 |
| RON | 95.8 | 95.3 | 94.5 | 95.6 | 95.1 |

The test results show that when using the product obtained by the process of the invention as an additive in a standard 95E gasoline, no significant change in the octane numbers was observed.

Example 4

The same turpentine feed as in Example 1 was used in this Example. The process parameters are summarized in Table 6 below. The catalyst was packed in two layers in the reactor, as in Example 2.

TABLE 6

| Feed | CST |
|---|---|
| Sulphur content (%) | about 1.5 |
| Pumping of feed ($V_{feed}$) (g/h) | 98 |
| Catalyst | NiMo/Al$_2$O$_3$ |
| Amount of catalyst (g) | 10 g (diluted) + 20 g (undiluted) |
| Reaction pressure (bar) | 30 |
| H$_2$ (l/h) | 25 |
| WHSV (h$^{-1}$) | 4.9 |
| Temperature of bed (° C.) | 405 |
| H$_2$ feed/turpentine feed (Nl/l) | 215 |

The composition of the product is shown in Table 7 below.

TABLE 7

| Polycyclic hydrocarbons (%) | 14.6 |
|---|---|
| Monocyclic hydrocarbons (%) | 21.3 |
| Acyclic hydrocarbons (%) | 7.9 |
| Aromatic hydrocarbons (%) | 48.0 |
| Others (%) | 8.2 |

The invention claimed is:

1. A process for producing fuel hydrocarbon components, said process comprising:

providing a terpene feed selected from a group consisting of crude sulphate turpentine derived from kraft pulping process of wood (CST), crude turpentine derived from mechanical pulping of wood, distillation bottoms from turpentine distillation, turpentine evaporated from crude tall oil, sulphur-containing C5 to C10 hydrocarbon streams from wood processing, and mixtures thereof, at a WHSV of about 0.5 to about 10, measured in accordance with the following equation:

$$WHSV[h^{-1}] = \frac{V_{feed[g/h]}}{m_{catalyst[g]}}$$

wherein $V_{feed[g/h]}$ means a pumping velocity of the terpene feed, and $M_{catalyst[g]}$ means an amount of the catalyst;

subjecting the terpene feed and a hydrogen gas, in a volumetric ratio of hydrogen gas to the terpene feed of from about 100 to about 1500 Nl/l, to a hydrogenation step at a temperature range of from about 275° C. to about 425° C. and at a pressure of 10 to 150 bar, in the presence of a hydrodesulphurization catalyst selected from a group consisting of NiO/MoO$_3$, CoO/MoO$_3$ and a mixture of NiO/MoO$_3$ and CoO/MoO$_3$ on a support selected from Al$_2$O$_3$ and Al$_2$O$_3$—SiO$_2$, to produce hydrocarbon components comprising C$_4$ to C$_{28}$ hydrocarbons; and recycling at least a portion of the hydrocarbon components back to the terpene feed and/or to the hydrogenation step.

2. The process of claim 1, wherein a sulphur feed is optionally fed to the hydrogenation step.

3. The process of claim 1, wherein the hydrocarbon components are subjected to separation to separate gasoline, diesel, naphtha and jet range hydrocarbon fractions.

4. The process of claim 1, wherein the hydrocarbon components are subjected to a hydrogen sulphide removal step to remove any residual hydrogen sulphide from the mixture.

5. The process of claim 1, wherein the residual hydrogen sulphide is removed by stripping, flashing or bubbling with inert gas.

6. The process of claim 1, wherein the hydrogenation step is carried out at a temperature of about 400° C.

7. The process of claim 1, wherein the hydrogenation step is carried out at a pressure of about 20 to about 70 bar.

8. The process of claim 1, wherein the hydrogenation step is carried out at a pressure of about 25 to about 50 bar.

9. The process of claim 1, wherein a volumetric ratio of H$_2$ gas fed to the hydrogenation step to the terpene feed is in the range from about 100 to about 350 Nl/l.

10. The process of claim 1, wherein a volumetric ratio of H$_2$ gas fed to the hydrogenation step to the terpene feed is in the range from about 100 to about 300 Nl/l.

11. The process of claim 1, wherein the WHSV is in the range of about 1 to about 5.5.

12. The process of claim 1, wherein a mixture of 1-isopropyl-4-methylbenzene, 1-isopropyl-4-methylcyclohexane and 2,6-dimethyloctane or isomers thereof is formed.

13. The process of claim 12, wherein WHSV is about 2 to about 3.5 and the temperature is greater than about 330° C.

14. The process of claim 12, wherein 1-isopropyl-4-methylbenzene is isolated.

15. The process of claim 1, wherein the hydrocarbon components obtained are fuel compositions or additives in fuel compositions.

16. The process of claim 15, wherein the fuel compositions are gasoline, diesel, naphtha or jet fuel.

17. The process of claim 1, wherein sulphur is supplied to the process and wherein the added amount of sulphur is in the range of about 100 to 200 ppm.

* * * * *